United States Patent
Floyd et al.

(10) Patent No.: US 6,248,927 B1
(45) Date of Patent: Jun. 19, 2001

(54) STABILIZED CYCLOBUTANONE COMPOSITIONS

(75) Inventors: Thomas Richard Floyd; Joseph Robert Zoeller; Paula Sue Cahill, all of Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/737,227

(22) Filed: Dec. 14, 2000

(51) Int. Cl.$^7$ .................................................. C07C 45/78
(52) U.S. Cl. ............................................................ 568/304
(58) Field of Search ...................................... 568/304, 309

(56) References Cited

U.S. PATENT DOCUMENTS 2,105,284 * 1/1938 Groll et al. .
2,687,962 * 8/1954 Chenicek .
2,770,545 * 11/1956 Thompson .
3,637,358 * 1/1972 Cyba .
5,874,631 * 2/1999 Ross et al. .

OTHER PUBLICATIONS

E. Lee–Ruff, Adv. Strain Org. Chem., (1991), 1, pp. 167–213 "New Synthetic Pathways from Cyclobutanones".
Bellus et al., Angew. Chem., (1988), 100 (6), pp. 820–850.
Bellus et al., Angew Chem Int. Ed. Engl., 27 (1988) pp. 797–825.
Krumpolc et al., Organic Synthesis Collective vol. VII, pp. 114–117.
M. N. Das et al., J. Amer. Chem. Soc., (1954), 76, pp. 6271–6274 "The Thermal Decomposition of Cyclobutanone".
T. H. McGee et al., Journal of Physical Chemistry, (1972), vol. 76, No. 7, pp. 963–967 "Thermal Decomposition of Cyclobutanone".
A. T. Blades, Can. J. Chem., (1969), vol. 47, pp. 615–617 "Kinetics of the Thermal Decomposition of Cyclobutanone".
R. A. Back et al., J. Chem. Phys., (1979), vol. 83, No. 16, pp. 2063–2064 "Effect of Oxygen on the Thermal Decomposition of Cyclobutanone".
J. Metcalfe et al., J. Amer. Chem. Soc., (1973), 95, pp. 4316–4320 "Thermal Decomposition of 2–Chlorocyclobutanone".
H. M. Frey et al, J. Chem. Soc., Perkin Trans. 2, (1977), pp. 752–753 "Thermal Decomposition of 3,3–Dimethylcyclobutanone".
A. H. Al–Husaini et al., Tetrahedron, (1991), vol. 47, No. 36, pp. 7719–7726 "Study of Ketene–Alkene Cycloadditions and Cycloreversions of Cyclobutanones".
H. O. Denschlug et al., J. Amer. Chem. Soc., (1967), 89, pp. 4795–4798 "On the Mechanism of the Photochemical Decomposition of Cylcobutanone in the gas Phase".
F. E. Blacet et al., J. Amer. Chem. Soc., (1957), 79, pp. 4327–4329 "The Photochemical Decomposition of Cyclohexanone Cyclopentanone & Cyclobutanone".

* cited by examiner

Primary Examiner—Johann Richter
Assistant Examiner—Sikarl A. Witherspoon
(74) Attorney, Agent, or Firm—Michael J. Blake; Harry J. Gwinnell

(57) ABSTRACT

Disclosed is a method for the stabilization of cyclobutanone compounds with a phenolic stabilizer compound and to stabilized compositions comprising a cyclobutanone compound and a phenolic stabilizer compound. The stabilization of cyclobutanone compounds with a phenolic stabilizer compound eliminates or minimizes the formation of a solid material when cyclobutanone compounds are stored and/or transported under ordinary shipping conditions.

12 Claims, No Drawings

STABILIZED CYCLOBUTANONE COMPOSITIONS

FIELD OF THE INVENTION

This invention pertains to a method for stabilizing cyclobutanone compounds and to stabilized cyclobutanone compositions. More specifically, this invention pertains to the stabilization of liquid cyclobutanone compounds with a phenolic stabilizer compound and to stabilized compositions comprising a liquid cyclobutanone compound and a phenolic stabilizer compound. The stabilization of cyclobutanone compounds with a phenolic stabilizer compound eliminates or minimizes the formation of a solid material when cyclobutanone compounds are stored and/or transported under ordinary shipping conditions.

BACKGROUND OF THE INVENTION

Cyclobutanone and its derivatives are useful intermediates in the preparation of a variety of organic compounds. For example see E. Lee-Ruff, *Adv. Strain Org. Chem*, (1991), 1, 167 and Bellus et al., *Angew Chem.*, (1988), 100(6), 820. Cyclobutanone itself can be prepared by the oxidation of cyclobutanol with chromium trioxide and oxalic acid in water as described, for example, by Krumpolic and Rocek in *Organic Synthesis Collective Volume VII*, pages 114–117. The chromium trioxide/oxalic acid oxidation is relatively non-selective and produces a dilute aqueous crude cyclobutanone mixture containing many hard-to-separate impurities. Typical impurities in the crude aqueous cyclobutanone include, but are not limited to, cyclopropanemethanol, unreacted cyclobutanol, 3-butene-1-ol, 2-butene-1-ol, cyclopropane carboxaldehyde, cyclopropane carboxylic acid, ethers and mixed ethers of cyclobutanol, cyclopropanemethanol, 3-butene-1-ol, and 2-butene-1-ol; hemi-ketals and ketals of the cyclopropanemethanol, cyclobutanol, 3-butene-1-ol and 2-butene-1-ol with cyclobutanone as well as other unknown compounds with boiling points higher and lower than cyclobutanone. Many of these impurities are color bodies and which cause the cyclobutanone product to be highly colored if not removed. Cyclobutanone having a purity of at least 99% may be obtained by a purification process comprising the steps of:

(1) distilling the aforesaid crude aqueous cyclobutanone product mixture to obtain (i) a distillate comprising cyclobutanone, water, cyclopropanemethanol, cyclobutanol, 3-butene-1-ol, 2-butene-1-ol, cyclopropane carboxaldehyde, ethers and mixed ethers of cyclobutanol, cyclopropanemethanol, 3-butene-1-ol, and 2-butene-1-ol, and hemi-ketals and ketals of cyclopropanemethanol, cyclobutanol, 3-butene-1-ol and 2-butene-1-ol with cyclobutanone; and (ii) a distillation residue comprising water, metal salts, and high boiling organic compounds such as $\gamma$-butyrolactone, cyclopropane carboxylic acid, and hemi-ketals and ketals of cyclopropanemethanol, cyclobutanol, 3-butene-1-ol and 2-butene-1-ol with cyclobutanone;

(2) allowing the resultant mixture to separate into (i) an organic phase comprising a minor amount of the cyclobutanone contained in the distillate and a major amount of impurities less soluble in water than cyclobutanone such as ethers, ketals, and color bodies; and (ii) an aqueous phase comprising water, a major amount of the cyclobutanone contained in the distillate, a minor amount of more hydrophilic impurities such as alcohols and cyclopropane carboxaldehyde;

(3) distilling the aqueous phase from step (2) to obtain (i) a minor amount of distillate comprising low-boiling azeotropes comprising water and organic impurities in the aqueous phase, (ii) a major amount of distillate comprising an azeotrope of water and cyclobutanone, and (iii) a distillation residue comprising water, cyclopropanecarboxylic acid, $\gamma$-butyrolactone, cyclobutanol, cyclopropanemethanol, mixed ethers of the alcohols, and ketals formed from reactions between ethers and alcohols;

(4) allowing distillate (ii) from step (3) to separate into (i) a cyclobutanonerich organic phase comprising cyclobutanone, water, and one or more aldehydes having boiling points close to that of cyclobutanone and (ii) an aqueous phase comprising cyclobutanone and water; and (5) distilling organic phase (i) from step (4) to obtain (i) a first distillate comprising an azeotrope of water and cyclobutanone, (ii) a second distillate comprising cyclobutanone having a purity of at least 90%, and (iii) a distillation residue comprising cyclobutanol, cyclopropanemethanol, mixed ethers of the alcohols, and ketals formed from reactions between ethers and alcohols.

The cyclobutanone product may contain an unacceptably high level of aldehydes, e.g., cyclopropane carboxaldehyde and cis/trans-croton-aldehyde, since such compounds are particularly difficult to remove during the purification process. The 5-step purification process described above may include an aldehyde conversion step wherein the distillations of steps (3) and/or (5) are preceded with an aldehyde conversion wherein the material to be distilled in steps (3) and/or (5) is treated with a material which converts the aldehyde to another compound or compounds having boiling points higher than the otherwise difficult-to-separate aldehydes. This ancillary step causes the aldehyde(s) present to be converted to products that have higher boiling points and, therefore, are readily separated from the cyclobutanone.

Even after meticulous purification according to the procedure described above, the cyclobutanone, which initially is obtained as a clear, colorless liquid of high purity, e.g., typically >99% pure, develops a fine, easily dispersed, white precipitate upon shipping and storage. The precipitate may form over time periods ranging from as short as several days to several months, depending upon storage and shipping conditions. The precipitate renders the material unsuitable for use, particularly in uses requiring high purity such as in the preparation of pharmaceutical compounds. The mode by which this precipitate is generated is not understood at this time, but appears to be inherent to highly purified cyclobutanone. Currently, the only way to extend the shelf life of this material is to store and ship the material under refrigeration in a darkened bottle. This adds significant expense and complications in shipping and handling without any assurance of long term stability.

Although the mode of precipitate formation is not clearly understood, others have described the thermal and photochemical degradation of cyclobutanone. See, for example, E. Lee-Ruff, *Adv. Strain Org. Chem*, (1991), 1, 167. Both the thermal and photochemical processes are believed to proceed by a common route involving the cleavage of the bond between the carbonyl and methylene unit with subsequent degradation of the diradical as shown below:

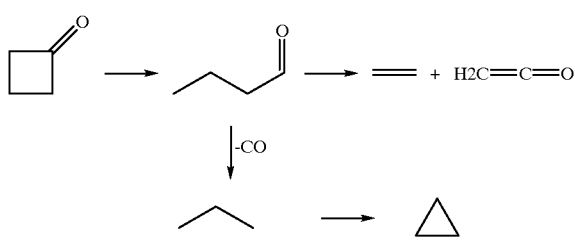

A more detailed description of the thermal decomposition of cyclobutanone can be found in M. N. Das, F. Kern, F. Cern, and T. D. Doyle, *J. Amer. Chem. Soc.*, (1954) 76, 6271–6274; T. H. McGee and A. Scheifler, *Journal of Physical Chemistry*, (1972) 76, pp. 963–967; and A. T. Blades, *Can. J. Chem.*, (1969) 41, 615–617. Decomposition temperatures for cyclobutanone in these studies are >360° C. The decomposition can be accelerated by the presence of oxygen, as described in R. A. Back and M. H. Back, *J. Chem. Phys.*, (1979) 83, 2063–2064. However, experiments carried out in the presence of oxygen were still performed at temperatures in excess of 270° C. Therefore, cyclobutanone normally would be regarded as thermally stable at normal storage and handling temperatures.

Thermal decomposition data for 2-chlorocyclobutanone have been reported by J. Metcalfe and E. K. C. Lee, *J. Amer. Chem. Soc.*, (1973) 95, 4316–4320 and for 3,3-dimethyl cyclobutanone by R. A. Smith, *J. Chem. Soc.*, Perkin Trans. 2, (1977) 752–753. Certain substitution, especially the presence of electron withdrawing groups, such as nitriles, esters, or keto groups in the 2-position can significantly lower the thermal stability of the substituted cyclobutanone as described by A. H. Al-Husianni, M. Muqtar, A. S. Asrof, Tetrahedron, (1991) 47, 7719–7126.

The photochemical decomposition of cyclobutanone is described by H. O. Denschlug and K. C. Lee, *J. Amer. Chem. Soc.*, (1967) 89, 4795 and by F. E. Blacet and A. Miller, *J. Amer. Chem. Soc.*, (1957) 79, 4327. The photochemical decomposition normally occurs with short wavelength UV irradiation, e.g., generally at wavelengths <313 nm, which is not ordinarily encountered upon storage and handling. In the case of both the photochemical and thermal decomposition paths, the studies normally are conducted in the vapor phase and, in the case of cyclobutanone, these processes yield a mixture of ethylene, ketene, cyclopropane, and carbon monoxide.

With only one notable exception, all these experiments were conducted in the vapor phase. In the lone exception, several simple cyclobutanone derivatives were examined by photochemical decomposition in methanolic solutions. In addition to the normally observed fragmentation products (olefin, CO, cyclopropanes, and ketenes), 2-methoxytetrahydrofurans also were observed. However, as already noted, the temperatures used in the thermal decomposition experiments reported in the literature and the wavelengths used in photolytic decomposition experiments normally are not encountered in typical storage, handling, and use of cyclobutanone compounds. Further, a method for stabilizing cyclobutanone compounds with regard to precipitate formation is presently not available. More generically, with the exception of α,β-unsaturated ketones, which are prone to olefin polymerization, ketones (including cyclic ketones) normally are considered to be stable with long shelf lives.

BRIEF SUMMARY OF THE INVENTION

We have now discovered that the addition of phenolic compounds, i.e., hydroxylated aromatic compounds, to cyclobutanone compounds inhibits, and usually eliminates, the formation of solid material in cyclobutanone compounds. Thus, a first embodiment of the present invention concerns a method for stabilizing a liquid cyclobutanone compound, i.e., inhibiting or preventing conversion of the cyclobutanone compound to a solid material, which comprises adding a phenolic stabilizer compound to the cyclobutanone compound. A second embodiment of the present invention concerns a stabilized composition comprising a liquid cyclobutanone compound and a phenolic stabilizer compound.

DETAILED DESCRIPTION

Examples of the liquid cyclobutanone compounds which may be used in the present invention have the following general formula:

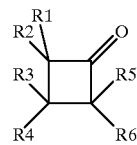

wherein $R^1$, $R^2$, $R^3$, $R^4$, $R^5$, and $R^6$ are independently selected from hydrogen, alkyl, cycloalkyl, aryl, hydroxyl; alkoxy, aryloxy, alkanoyloxy, carboxy, alkanoyl, alkoxycarbonyl, halogens and cyano. Unsubstituted cyclobutanone presently is the most valuable and thus the most preferred of the cyclobutanone compounds which may be stabilized in accordance with the present invention.

The cyclobutanone compounds which may be stabilized in accordance with the present invention include unsubstituted cyclobutanone and cyclobutanone substituted with alkyl, cycloalkyl, aryl, hydroxy, alkoxy, aryloxy, carboxy, alkanoyl, alkanoyloxy, alkoxycarbonyl, halogen, cyano, and the like. The alkyl substituents may be straight- or branched-chain, saturated, aliphatic hydrocarbon radicals containing one to six carbon atoms. The cycloalkyl groups include saturated, carbocyclic, hydrocarbon radicals having three to eight carbon optionally substituted with one to three $C_1$–$C_6$-alkyl group(s). Examples of the aryl substituents and the aryl moiety of the aryloxy substituents include phenyl and phenyl substituted with one to three substituents selected from $C_1$–$C_6$-alkyl, substituted $C_1$–$C_6$-alkyl, $C_1$–$C_6$-alkoxy, halogen, carboxy, cyano, $C_2$–$C_6$-alkanoyloxy, $C_1$–$C_6$-alkylthio, $C_1$–$C_6$-alkylsulfonyl, trifluoromethyl, hydroxy, optionally substituted sulfamoyl, $C_2$–$C_6$-alkoxycarbonyl, and $C_2$–$C_6$-alkanoylamino. The term halogen is used to include fluorine, chlorine, bromine, and iodine. The alkoxy, alkoxycarbonyl, alkanoyloxy and alkanoyl groups have the general formulas —OR, —$CO_2$R, —OCOR and —COR, respectively, wherein R is $C_1$–$C_6$-alkyl or substituted $C_1$–$C_6$-alkyl.

The phenolic stabilizer compound may be selected from a wide variety of hydroxylated and polyhydroxylated aromatic compounds described in the literature. Examples of preferred phenolic stabilizer compounds include those having the general formula:

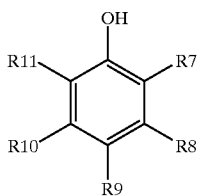

wherein $R^7$, $R^8$, $R^9$, $R^{10}$, and $R^{11}$ are independently selected from alkyl, aryl, hydroxy, alkoxy, aryloxy, alkanoyloxy, carboxy and alkoxycarbonyl, and wherein $R^7$, $R^8$, $R^{10}$, and $R^{11}$ may additionally be independentally selected from hydrogen. Examples of the foregoing substituents are provided above relative to groups represented by $R^1$–$R^6$. These groups may be present in any combination and may be part of a fused ring structure. However, the preferred inhibitors are chosen from the class wherein $R^7$ and $R^{11}$ are selected from methyl, $C_4$–$C_8$-tert-alkyl such as tert-butyl, hydrogen, or hydroxy, $R^8$ and $R^{10}$ are selected from $C_4$–$C_8$-tert-alkyl, or hydrogen, and $R^9$ is selected from hydroxy, methoxy, $C_2$–$C_4$ alkoxycarbonyl, and methyl. These are readily available commercially and effective.

Phenolic stabilizer compounds which are non-toxic and approved for a wide variety of applications, such as food additives, represent a preferred group of phenolic stabilizers since cyclobutanone compounds stabilized with such phenolic compounds have a broad variety of end uses. Therefore, the more preferred phenolic stabilizer compounds are selected from the group of inhibitors that are recognized as safe for use as food grade inhibitors and antioxidants. This group includes 2,6-di-tert-butyl 4-methylphenol (butylated hydroxytoluene-BHT), a mixture of 2-tert-butyl-4-hydroxyanisole and 3-tert-butyl-4-hydroxyanisole (butylated hydroxyanisole-BHA), n-propyl 3,4,5-trihydroxybenzoate (propyl gallate), and tert-butyl-hydroquinone (tBHQ). BHT is especially preferred. It will be apparent to those skilled in the art that the phenolic stabilizer compounds may be used individually or in combination.

The stabilizing-effective amount of the phenolic compound may vary significantly depending, for example, on the particular phenolic compound employed and the conditions, e.g., time and temperature, over which the cyclobutanone compound requires stabilization. The concentrations of the phenolic compound may be as low as 5 parts per million by weight (ppmw) and as high as 1 weight percent, based on the weight of the cyclobutanone compound. Although stabilizer concentrations as high as 1 weight percent may be required for very unstable cyclobutanone compounds, for most compounds such high levels can be undesirable due to unacceptable contamination of the cyclobutanone compound which may limit or preclude its use for certain purposes. Therefore, generally modest levels, e.g., about 10 to 500 ppmw, provide adequate stabilization for most cyclobutanone compounds and, especially, unsubstituted cyclobutanone. The preferred concentration of the phenolic stabilizer compound is in the range of about 25 to 250 ppmw, again based on the weight of the cyclobutanone compound.

EXAMPLES

The operation of the novel method and preparation of the novel compositions provided by the present invention are further illustrated by the following examples.

The cyclobutanone employed in the experiments described below was prepared according to the procedure described by Krumpolic and Rocek in *Organic Synthesis Collective Volume* VII, pages 114–117. The crude cyclobutanone was purified by the procedure described above to obtain cyclobutanone having a purity of >99% and subjected to further purification by (1) filtration through a fine frittered glass filter or celite to remove all existing precipitate followed by (2) redistillation of the cyclobutanone taking a fraction that removed a 10% forecut, which was discarded, and then removing about 70% of the remaining cyclobutanone. (B.P. 98° C.).

The purified cyclobutanone was stabilized by dissolving 200 mg of the phenolic stabilizer in 20 grams of the purified cyclobutanone to generate a stock solution of stabilizer in cyclobutanone. Further dilution to give a 200 ppmw solution of stabilizer in cyclobutanone was accomplished by dissolving 0.2 g of the stock solution in 10 mL of purified cyclobutanone. Cyclobutanone solutions containing 200 ppm of stabilizer were prepared in duplicate for each stabilizer.

To evaluate the stabilization of the cyclobutanone, both samples of stabilizer/cyclobutanone solution were subjected to an accelerated precipitation test in which the stabilized cyclobutanone solution was placed in an oven maintained at 45° C. (113° F.). Control or comparison samples without stabilizer were taken from the same purified sample of cyclobutanone and placed in the oven at the same time.

The first sample of stabilized cyclobutanone and a sample of unstabilized cyclobutanone for comparison were removed simultaneously after 2 weeks of heating at 45° C. The second sample of stabilized cyclobutanone, as well as a second sample of unstabilized cyclobutanone for comparison, was removed after 4 weeks heating at 45° C. The visual appearance of each sample was recorded and the turbidity, a measure of the suspended solids, was measured using a Hach Ratio Turbidimeter, Model 18900, and recorded in Nepholometric Turbity Units (NTU). Since stabilizers may or may not impart a yellow tint when used in the stabilization of cyclobutanone, the yellow index of each of the stabilized samples was measured using ASTM method E313 and D1925. For comparison purposes, a fresh sample of cyclobutanone demonstrates a turbidity of 0.3 NTU and a yellow index of 1.9 for ASTM E313 and 1.7 for ASTM Method D1925.

Example 1

Stabilized cyclobutanone solutions containing 200 ppmw of 2,6-di-tert-butyl 4-methyl phenol (BHT) were prepared and subjected to the accelerated aging test as described above. BHT gives superior stabilization toward precipitate (solids) formation with no detectable color formation.

Example 2

Example 1 was repeated except BHA (a mixture of 2-tert-butyl-4-hydroxyanisole and 3-tert-butyl-4-hydroxyanisole) was used in place of BHT. BHA demonstrates superior stabilization toward precipitate formation but displays some color formation as indicated by ASTM methods E313 and D1925, even though the color is not easily observed by visual inspection.

Example 3

Example 1 was repeated except propyl gallate (n-propyl 3,4,5-trihydroxy benzoate) was used in place of BHT. Propyl gallate (PG) demonstrates superior stabilization and statistically insignificant color formation.

Example 4

Example 1 was repeated except tert-butyl hydroquinone (tBHQ) was used in place of BHT. It should be noted that tBHQ, while giving cyclobutanone solutions that are stable toward precipitation, gives solutions that are observably yellow, and clearly less preferred as a stabilizer.

Comparative Example C-1

Example 1 was repeated except BHT was completely omitted. These experiments represent the control or comparison samples referred to in the general procedure described above. The solutions are not obviously colored but have generated quite noticeable levels of precipitate.

The visual inspections and instrument values determined for the various stabilized and unstabilized cyclobutanone samples used in the preceding examples are shown in Table I wherein BHT, BHA, PG and tBHQ have the meanings given above, the values given for Turbidity are Nepholometric Turbity Units determined as described above, and the number of Weeks refers to the time in weeks during which the particular sample had been subjected to the above-described accelerated precipitation test.

TABLE I

| Example No. | Stabilizer | Appearance | Turbidity 2 Weeks | Turbidity 4 Weeks | Yellow Index ASTM E313 2 Weeks | ASTM E313 4 Weeks | ASTM D1925 2 Weeks | ASTM D1925 4 Weeks |
|---|---|---|---|---|---|---|---|---|
| 1 | BHT | Cloudy, colorless | 0.2 | 0.1 | 1.8 | 1.8 | 1.6 | 1.5 |
| 2 | BHA | Clear, colorless | 0.5 | 0.1 | 2.4 | 3.3 | 2.2 | 3.2 |
| 3 | PG | Clear colorless | 0.5 | 0.1 | 2.0 | 2.0 | 1.8 | 1.9 |
| 4 | tBHQ | Clear, yellow | 0.4 | 0.2 | 10.2 | 14.6 | 10.8 | 15.7 |
| C-1 | None | Cloudy Colorless | 3.4 | 5.1 | — | 3.8* | — | 3.6* |

*Value uncertain due to large volume of solids.

Examples 5–7 and C-2 demonstrate the effectiveness of lower amounts of stabilizer over an even longer time periods (54 days).

Example 5

Example 1 was repeated except the aging test was performed for 54 days.

Example 6

Example 5 was repeated except that the quantity of BHT stock solution used in the final dilution was reduced to 0.1 g, yielding a solution containing only 100 ppmw of BHT in cyclobutanone.

Example 7

Example 5 was repeated except that the quantity of BHT stock solution used in the final dilution was reduced to 0.05 g, yielding a solution containing only 50 ppmw of BHT in cyclobutanone.

Comparative Example C-2

Comparitive Example C-1 was repeated except that the test period was 54 days.

The results obtained in Examples 5–7 and Comparative Example C-2 are summarized in Table II.

TABLE II

| Example No. | BHT Level (PPMW) | Appearance | Turbidity (NTU) | Yellow Index ASTM E313 | Yellow Index ASTM D1925 |
|---|---|---|---|---|---|
| C-2 | None | Cloudy, yellow tinge | 6.4 | 4.4 | 4.1 |
| 5 | 200 | Clear, colorless | 0.1 | 2.3 | 2.1 |
| 6 | 100 | Clear, colorless | 0.1 | 2.3 | 2.1 |
| 7 | 50 | Clear, colorless | 0.2 | 2.3 | 2.2 |

The invention has been described in detail with particular reference to preferred embodiments thereof, but it will be understood that variations and modifications can be effected within the spirit and scope of the invention.

We claim:

1. Method for stabilizing a liquid cyclobutanone compound which comprises adding a phenolic stabilizer compound to the cyclobutanone compound wherein the phenolic stabilizer has the general formula:

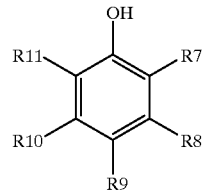

wherein $R^7$, $R^8$, $R^9$, $R^{10}$, and $R^{11}$ are independently selected from alkyl, aryl, hydroxy, alkoxy, aryloxy, alkanoyloxy, carboxy and alkoxycarbonyl; and $R^7$, $R^8$, $R^{10}$, and $R^{11}$ may additionally be independently selected from hydrogen.

2. Method according to claim 1 wherein the phenolic stabilizer has the general formula:

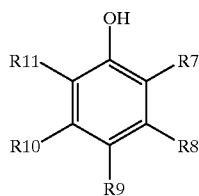

wherein $R^7$ and $R^{11}$ are selected from methyl, $C_4$–$C_8$-tert-alkyl, hydrogen, or hydroxy, $R^8$ and $R^{10}$ are selected from $C_4$–$C_8$-tert-alkyl, or hydrogen, and $R^9$ is selected from hydroxy, methoxy, $C_2$–$C_4$ alkoxycarbonyl, and methyl; and the amount of the phenolic stabilizer added is 10 to 500 ppmw.

3. Method according to claim 2 wherein the phenolic stabilizer is 2,6-di-tert-butyl 4-methylphenol, a mixture of 2-tert-butyl-4-hydroxyanisole and 3-tert-butyl-4-hydroxyanisole, n-propyl 3,4,5-trihydroxybenzoate, or tert-butylhydroquinone.

4. A stabilized composition comprising a liquid cyclobutanone compound and a phenolic stabilizer wherein the phenolic stabilizer has the general formula:

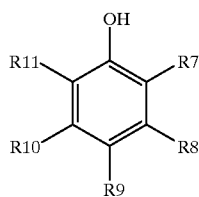

wherein $R^7$, $R^8$, $R^9$, $R^{10}$, and $R^{11}$ are independently selected from alkyl, aryl, hydroxy, alkoxy, aryloxy, alkanoyloxy, carboxy and alkoxycarbonyl; and $R^7$, $R^8$, $R^{10}$, and $R^{11}$ may additionally be independently selected from hydrogen.

5. A stabilized composition according to claim 4 wherein the phenolic stabilizer has the general formula:

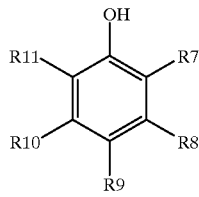

wherein $R^7$ and $R^{11}$ are selected from methyl, $C_4$–$C_8$-tert-alkyl, hydrogen, or hydroxy, $R^8$ and $R^{10}$ are selected from $C_4$–$C_8$-tert-alkyl, or hydrogen, and $R^9$ is selected from hydroxy, methoxy, $C_2$–$C_4$ alkoxycarbonyl, and methyl; and the amount of the phenolic stabilizer present is 10 to 500 ppmw.

6. A stabilized composition according to claim 5 wherein the phenolic stabilizer is 2,6-di-tert-butyl 4-methylphenol, a mixture of 2-tert-butyl-4-hydroxyanisole and 3-tert-butyl-4-hydroxyanisole, n-propyl 3,4,5-trihydroxy-benzoate, or tert-butylhydroquinone.

7. Method for stabilizing cyclobutanone which comprises adding a phenolic stabilizer compound to the cyclobutanone wherein the phenolic stabilizer has the general formula:

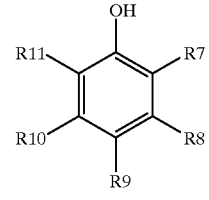

wherein $R^7$, $R^8$, $R^9$, $R^{10}$, and $R^{11}$ are independently selected from alkyl, aryl, hydroxy, alkoxy, aryloxy, alkanoyloxy, carboxy and alkoxycarbonyl; and $R^7$, $R^8$, $R^{10}$, and $R^{11}$ may additionally be independently selected from hydrogen.

8. Method according to claim 7 wherein the phenolic stabilizer is 2,6-di-tert-butyl 4-methylphenol, a mixture of 2-tert-butyl-4-hydroxyanisole and 3-tert-butyl-4-hydroxyanisole, n-propyl 3,4,5-trihydroxybenzoate, or tert-butylhydroquinone; and the amount of the phenolic stabilizer added is 10 to 500 ppmw.

9. Method according to claim 7 wherein the phenolic stabilizer is 2,6-di-tert-butyl 4-methylphenol; and the amount of the phenolic stabilizer added is 25 to 250 ppmw.

10. A stabilized composition comprising cyclobutanone and a phenolic stabilizer compound wherein the phenolic stabilizer has the general formula:

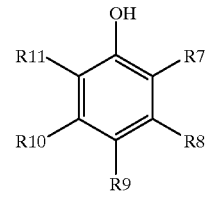

wherein $R^7$, $R^8$, $R^9$, $R^{10}$, and $R^{11}$ are independently selected from alkyl, aryl, hydroxy, alkoxy, aryloxy, alkanoyloxy, carboxy and alkoxycarbonyl; and $R^7$, $R^8$, $R^{10}$, and $R^{11}$ may additionally be independently selected from hydrogen.

11. A stabilized composition according to claim 10 wherein the phenolic stabilizer is 2,6-di-tert-butyl 4-methylphenol, a mixture of 2-tert-butyl-4-hydroxyanisole and 3-tert-butyl-4-hydroxyanisole, n-propyl 3,4,5-trihydroxybenzoate, or tert-butyl-hydroquinone; and the amount of the phenolic stabilizer added is 10 to 500 pp mw.

12. A stabilized composition according to claim 10 wherein the phenolic stabilizer is 2,6-di-tert-butyl 4-methylphenol; and the amount of the phenolic stabilizer added is 25 to 250 ppmw.

\* \* \* \* \*